United States Patent [19]

Feuchter et al.

[11] Patent Number: 5,250,417
[45] Date of Patent: Oct. 5, 1993

[54] METHOD FOR ACROSOME REACTION ASSAY

[75] Inventors: Frederick A. Feuchter; Buck A. Rhodes, both of Albuquerque, N. Mex.

[73] Assignee: Rhomed Incorporated, Albuquerque, N. Mex.

[21] Appl. No.: 690,526

[22] Filed: Apr. 23, 1991

[51] Int. Cl.$^5$ ............................ C12Q 1/37; C12Q 1/02
[52] U.S. Cl. ........................................ 435/23; 435/29; 435/806; 436/906
[58] Field of Search ........................ 435/23, 29, 806, 2; 436/906

[56] References Cited

U.S. PATENT DOCUMENTS 4,767,703  8/1988  Ax et al. ................................ 435/29

FOREIGN PATENT DOCUMENTS

WO89/02743  4/1989  United Kingdom .

OTHER PUBLICATIONS

Wolf D. P. Acrosomal Status Evaluation in Human ... Biology of Reproduction 32: 1157–1162 1985.
Cross Two Simple Methods for Detecting Acrosome Reacted Sperm, Gamete Research 15: 213–226 1986.
Dandekar et al. Electron Microscope Evaluation of Rabbit Eggs J. Reprod Fert 44: 143–146 1974.
Shulman Studies in Local Immunity to Sperm ... Am Reprod Immunol 1:49–52 1980.
I. Tummon, et al., "Acrosin Activity Correlates with Fertilization in Vitro," Abstract No. 81, J. Andrology, Sixteenth Annual Meeting, vol. 11 (Suppl.), p. 45 (1991).
S. A. Carson et al. (1988) "Antibody binding patterns in infertile males ... " Fertility and Sterility 49:487–492.
T. F. Kruger et al. (1988) "Predictive value of abnormal sperm morphology . . . " Fertility and Sterility 49:112–117.
G. N. Clarke et al. (1988) "Sperm antibodies and human in vitro fertilization" Fertility and Sterility 49:1018–1025.
S. L. Corson et al. (1988) "The human sperm–hamster egg ... " Fertility and Sterility 49:328–334.
Byrd and Wolf (1988) "Acrosomal status in fresh and capacited human ... " Biology of Reproduction 34:859–869.
Sathananthan and Chen (1986) "Sperm–oocyte membrane fusion ... " Gamete Research 15:177–186.
J. M. Bedford (1970) "Sperm Capacitation and Fertilization in Mammals" Biol Reprod (Suppl) 2:128–158.
Lee et al. (1987) "Capacitation and acrosome reactions in human spermatozoa ... " Fertility and Sterility 48:649–658.
Suarez et al. (1986) "Induction of the acrosome reaction in human ... " Gamete Research 14:107–121.
Feuchter et al. (1987) "The human sperm acrosome reaction ... " Anatomical Record 218:44A.
Kallajoki et al. (1986) "The fate of acrosomal staining during the acrosome ... " Int. J Andrology 9:181–194.
Parrish et al. (1980) "Glycosaminoglycan stimulation of the in vitro ... " J. Androl 1:89–95.
Aitken, et al. (1984) "Analysis of Human Sperm Function Following Exposure to the Ionophore A23187-:Comparison of Normospermic and Oligozoospermic Men" Journal of Andrology; vol. 5, pp. 321–329.

(List continued on next page.)

Primary Examiner—Michael G. Wityshyn
Assistant Examiner—Ralph Gitomer
Attorney, Agent, or Firm—Deborah A. Peacock; Donovan F. Duggan

[57] ABSTRACT

A method is provided for rapidly determining the ability of sperm to undergo the acrosome reaction, using fluorescence microscopy, light microscopy or color change on a dot blot assay to determine the relative percentage of acrosome reacted sperm. Sperm are capacitated through use of bromelain or other enzymatic substances capable of capacitating sperm, with the total incubation time required to induce capacitation as little as fifteen minutes, yielding sperm that are fully capacitated and show excellent motility, with as many as 80% of normal sperm consistently induced to acrosome react.

24 Claims, No Drawings

OTHER PUE

Bryan and Akruk (1977) "A Naphthol Yellow S and . . ." Stain Technol 52:47–50.

L. Dennison et al. (1991) Sperm Acrosome Reaction and Seminal Morphology . . . , J Andrology 11:P-31 (Suppl).

A. Agarwal et al. (1991) Acrosin Activity in Patients with Idiopathic Infertility, J. Andrology 11:P-32 (Suppl).

Meuli, L. E. et al. Improved Method for Detection for the Acrosome Reaction, J. Andrology 11:P-45 (Suppl) 1991.

P. Fenichel et al., "Dynamics of human sperm acrosome reaction relation with in vitro" . . . (1991) Fertil Steril 55:994–999.

J. M. Cummins et al. (1991), "A Test of the Human Sperm Acrosome Reaction . . . ," J Andrology 12:98–103.

The Merck Index, Merck & Co., Rahway, N.J. 10th Ed 1983 #1360.

METHOD FOR ACROSOME REACTION ASSAY

BACKGROUND OF THE INVENTION

1. Field of the Invention (Technical Field)

The present invention relates to the detection and measurement of the ability of sperm to undergo the acrosome reaction, and thereby permits determination of the fertility of male mammals in general.

2. Description of the Related Art, Including Information Disclosed under 37 C.F.R. Sections 1.97-1.99 (Background Art)

With the development of new and effective techniques of birth control, attention has become more focused on the converse problem, infertility. One out of six couples of child bearing age is affected by infertility, and about 40% of these cases are related to problems in the male. Female infertility problems have been systematically addressed for a number of years, but there are relatively few clinical tests relating to male infertility and its causes, other than an examination of sperm count, sperm morphology, and presence of anti-sperm antibodies. S. A. Carson et al (1988) "Antibody binding patterns in infertile males and females as detected by immunobead test, gel-agglutination test, and sperm immobilization test" *Fertility and Sterility* 49:487-492 and T. F. Kruger et al (1988) "Predictive value of abnormal sperm morphology in in vitro fertilization" *Fertility and Sterility* 49:112-117. In clinical assessment of male infertility, most of the standard tests currently performed in semen analysis detect only the most obvious defects. More recent developments include computer assisted semen analysis (CASA), the hamster ova penetration assay (SPA), and the hypo-osmotic swelling tests (HOS). The value of these kinds of tests for predicting fertility of patients is still being analyzed. The ultimate test of human sperm fertility is its ability to penetrate the human oocyte. The functional defects underlying individual infertility problems in many cases remain undiscovered.

In attempting to determine the causes of male infertility, physicians examine spermatozoa for their number, morphology, and forward motility characteristics. They also look for the presence of anti-sperm antibodies which may interfere with fertilization. Although these tests may be marginally useful, they detect only the most obvious defects of sperm, and only a small percentage of infertility cases are attributable to gross defects or to antibodies. Thus, the value of these kinds of tests in predicting potential fertility of patients is questionable. Many cases of unexplained infertility exist in which the above parameters are all within normal limits, yet sperm are incapable of fertilizing an ovum. The standard tests currently performed in semen analysis do not address sperm function in a direct manner. The functional defects underlying individual infertility problems in many cases remain undiscovered. In addition, the tests are time consuming and somewhat expensive to perform, requiring highly trained technologists and expensive equipment.

An exception to this generalization is the sperm-cervical mucus interaction test (SCMI), which examines the ability of a husband's sperm to penetrate his partner's cervical mucus, a critical step in the transport of sperm to the site of fertilization. G. N. Clarke et al (1988) "Sperm antibodies and human in vitro fertilization" *Fertility and Sterility* 49:1018-1025. This test of sperm function has only recently been performed on a routine basis and is useful in assessing certain types of infertility. Another functional test developed recently is the sperm penetration assay (SPA), in which sperm are examined for their ability to penetrate hamster ova which have been denuded of their zona pellucida. S. L. Corson et al (1988) "The human sperm-hamster egg penetration assay: prognostic value" *Fertility and Sterility* 49:328-334. The test has limited predictive value, since sperm are left in contact with the eggs for several hours, and zona-free ova are not physiologically relevant to actual fertilization; in fact, penetration of the zona pellucida surrounding the ovum is one of the critical steps in the fertilization process. D. P. Wolf et al (1985) "Acrosomal status evaluation in human ejaculated sperm with monoclonal antibodies" *Biology of Reproduction* 32:1157-1162. Both tests, the SCMI and SPA, require highly trained technologists, well-equipped laboratories, and several hours to perform.

Human male infertility can be attributed to two basic types of dysfunctions; those which are intrinsic to the sperm and result in defective sperm or sperm production, and those which are extrinsic to sperm, such as antibodies, which affect sperm function as a result of their interaction with sperm. Both types of defects may inhibit the acrosome reaction. The acrosome reaction is a critical process by which sperm release hydrolytic enzymes that degrade the zona pellucida, a thick protein and polysaccharide protective coating that surrounds the ovum. Penetration of the zona enables the sperm and ovum to come into contact, fuse, and complete the fertilization process. W. Byrd and D. P. Wolf (1988) "Acrosomal status in fresh and capacitated human ejaculated sperm" *Biology of Reproduction* 34:859-869; A. H. Sathananthan and C. Chen (1986) "Sperm-oocyte membrane fusion in the human during monospermic fertilization" *Gamete Research* 15:177-186.

The acrosome reaction is thought to be stimulated by contact with, or binding to, the zona pellucida, which induces a rise in the intracellular calcium level of the sperm. The rise in intracellular calcium in turn triggers the release of the hydrolytic enzymes, which leads to degradation of zona proteins. The ability to undergo the acrosome reaction and penetrate the zona pellucida is an absolute requirement for fertilization. Sperm may be defective in this ability as the result of a genetic defect, such as in round-headed sperm syndrome in which the acrosome is absent, or as the result of extrinsic factors such as sperm-coating antibodies which bind the sperm and prevent release of acrosomal contents. Currently, these defects can only be detected by electron microscopy or immunofluorescence and radioimmunoassay.

Spermatozoa undergo two steps in the acrosome reaction process: a reversible capacitation step followed by the irreversible acrosome reaction. The acrosome reaction enables sperm to penetrate the acellular glycoprotein layer, the zona pellucida, of the ovum. J. M. Bedford (1970) "Sperm Capacitation and Fertilization in Mammals" *Biol Reprod* (*Suppl*) 2:128-158. Capacitation in vivo is a little understood process that occurs to the sperm over a several hour period in the female reproductive tract after entry into the uterus. It is thought to involve, among other things, the removal of protein factors present in the seminal plasma which adhere to the sperm surface and prevent premature release of the acrosome. In research procedures, sperm can be capitated by incubation in physiologic saline for at least four hours. After this time, 30% to 50% of sperm undergo the acrosome reaction upon addition of calcium and its appropriate ionophore.

The ability of human spermatozoa to undergo the acrosome reaction is critical to the fertilization process. A variety of assays have been developed; however, each presents significant limitations. M. A. Lee, et al (1987) "Capacitation and acrosome reactions in human spermatozoa monitored by a chlortetracycline fluorescence assay" *Fertility and Sterility* 48:649-658; S. S. Suarez et al (1986) "Induction of the acrosome reaction in human spermatozoa by a fraction of human follicular fluid" *Gamete Research* 14:107-121; F. A. Feuchter et al (1987), "The human sperm acrosome reaction: involvement of a vimentin-associated surface glycoprotein of the equatorial segment" *Anatomical Record* 218:44A; N. L. Cross et al (1986) "Two simple methods for detecting acrosome-reacted human sperm" *Gamete Research* 15:213-226; and, M. Kallajoki et al (1986) "The fate of acrosomal staining during the acrosome reaction of human spermatozoa as revealed by a monoclonal antibody and PNA-lectin" *Int J Andrology* 9:181-194. Each assay requires a significant period of time to perform, particularly induction of capacitation, and no assay has been reduced to a simple dot-blot format.

Other methods of in vitro capacitation of sperm have been studied. Glycosaminoglycans have been shown to accelerate conversion of proacrosin to acrosin, thought to be a step in the induction of the acrosome reaction. R. F. Parrish et al (1980) "Glycosaminoglycan stimulation of the in vitro conversion of boar proacrosin into acrosin" *J Androl* 1:89-95.

A mixture of proteolytic enzymes, containing trypsin, chymotrypsin and $\beta$-amylase, has been used to strip the surface coat of rabbit sperm and induce capacitation in vitro. P. V. Dandekar and M. Gordon (1974) "Electron microscope evaluation of rabbit eggs exposed to spermatozoa treated with capacitating agents." *J Reprod Fert* 44:143-146. Unlike human sperm, rabbit sperm do not capacitate well in physiologic saline and must be enzyme-treated before a significant number will acrosome react when mixed with rabbit ova.

It is generally assumed that elevation of calcium ions in the cytoplasm between the plasma and outer acrosomal membranes is the key event in initiation of the acrosomal reaction. Capacitation thus involves the preparation of the sperm for the elevation in calcium ions. One method used for several years in mammalian sperm research employs a calcium ionophore to induce the acrosome reaction. This method mimics the natural process in which contact with the zona pellucida induces a rise in the intracellular calcium level of sperm, which in turn triggers the acrosome reaction. The ionophore is effective at inducing the acrosome reaction in properly capacitated and fertile sperm, but has no effect on oligozoospermic and otherwise infertile samples. R. J. Aitken (1984) Analysis of Human Sperm Function Following Exposure to the Ionophore A23187: Comparison of Normospermic and Oligozoospermic Men.

Once the acrosome reaction has been induced, there are a number of markers which can be used to detect and measure the percentage of spermatozoa undergoing the acrosome reaction. Lectin molecules can be used as markers of the human acrosome. Peanut agglutinin (PNA) and Pisum sativum agglutinin (PSA) are now recognized as markers of the acrosomal region of human sperm. Cross, supra, and Kallajoki, supra. PSA binds specifically to acrosomal contents, and PNA binds either to acrosomal contents or acrosomal membranes. Only acrosome intact sperm bind to the lectins, and sperm that have undergone the acrosome reaction do not bind the lectins. On sperm which are capable of undergoing the acrosome reaction, the acrosomal markers are shed and can be identified in the supernatant solution; on those which are incapable of the reaction, the markers are retained (or if genetically absent, no markers are shed) and are not identifiable in the supernatant solution. PNA appears to be pan-specific in its reactivity with the acrosome, that is, it can be used in species other than human.

Acrosomal staining can also be accomplished by the methods of J. H. D. Bryan and S. R. Akruk (1977) "A Naphthol Yellow S and Erythrosin B Staining Procedure for use in Studies of the Acrosome Reaction of Rabbit Spermatozoa" *Stain Technol* 52:47-50. In addition, methods have been developed for staining using monoclonal antibodies specific for acrosomal markers. Kallajoki, supra. Monoclonal antibodies are highly specific markers, and are useful for some techniques. However, they are not without limitations when used for probes of the acrosome reaction. Monoclonal antibodies are species specific, and thus lack pan-species applicability. In addition, monoclonal antibodies often exhibit low avidity, and not infrequently have a short shelf-life. Monoclonal antibodies are expensive to produce, and must be obtained from specialized laboratories. Other methods are also known to those skilled in the art.

R. L. Ax and R. W. Lenz, U.S. Pat. No. 4,767,703, *Method for Assessing the Fertility of Male Mammals* used a glycosaminoglycan to induce an acrosome reaction in sperm. A representative sample of incubated sperm from both the individual to be tested and a control are then stained and counted by means of observation by light microscopy to measure the increase in acrosome reaction in the test portion as compared to the control portion. This method requires a lengthy incubation of sperm in the glycosaminoglycan to induce the acrosome reaction; nine to twenty-two hours incubation are reported in the method.

J. A. Houghton, Patent Cooperation Treaty International Patent Application No. WO89/02743 (filed Sep. 23, 1988), *In Vitro Method for the Induction of the Spermatozoal Acrosome Reaction and Application of Said Method to the Assessment of Spermatozoa and the Treatment of Male-Related Infertility* subjects spermatozoa to electropermeabilisation involving application of an electric field sufficient to raise the spermatozoal plasma membrane potential from about −70 mV to +1 V to allow an influx of calcium ions. This method thus requires specialized equipment to induce the reaction. The method also induces a reaction even in sperm incapable of naturally undergoing the acrosome reaction, and thus is of limited utility in any diagnostic assay.

There is no known method of conducting both a microscopic and dot blot assay to examine the ability of human spermatozoa to undergo the acrosome reaction. These assays address a function of sperm that is critical to the fertilization process and which is not currently tested in clinical laboratories.

SUMMARY OF THE INVENTION (Disclosure of the Invention)

In accordance with the present invention, a method is provided for rapidly determining the ability of sperm to undergo the acrosome reaction, using either microscopy or a dot blot assay; for quickly inducing capacitation; and providing a format that is both convenient and requires a low level of skill to perform.

In the preferred embodiment for evaluating the ability of sperm of male mammals to undergo the acrosome reaction, a sperm sample is first obtained from the male mammal. The method applies to sperm of humans and other mammals, including domesticated livestock. A semen sample is obtained from the male mammal, and by using any means known in the art, the sperm is separated from the seminal plasma. Conventionally, this is done by allowing the sperm sample to liquify, by sitting at room temperature for a period of approximately 30 minutes, followed by dilution with appropriate reagents and centrifugation, with the sperm to be found in the resulting pellet.

The sperm is then incubated in a bromelain enzyme containing solution in a concentration effective to induce capacitation in the sperm. The bromelain enzyme containing solution optimally contains bromelain at a concentration of approximately 0.05%, and may further contain one or more proteolytic enzymes. The bromelain and optional proteolytic enzymes are in a solution of calcium ion free modified Tyrode's solution. The total incubation time optimally does not exceed approximately fifteen minutes.

The capacitated sperm are then incubated in a solution containing a calcium ionophore in a concentration effective to induce an acrosome reaction in the capacitated sperm. A representative sample of incubated capacitated sperm can then be examined to determine the ability of sperm of the male mammal to undergo the acrosome reaction.

Different indicator systems may be used to evaluate the ability of sperm of male mammals to undergo the acrosome reaction, including fluorescence microscopy. For fluorescence microscopy, the capacitated sperm is stained with an acrosome specific fluoroscein marker and examined using fluorescence microscopy. With this method, it is possible to count a representative sample of incubated capacitated sperm to measure the ability of sperm of the male mammal to undergo the acrosome reaction, and thereby achieve quantitative results. A variety of acrosome specific fluoroscein markers may be employed; the preferred acrosome specific fluoroscein markers include fluoroscein conjugated peanut agglutinin, fluoroscein conjugated Pisum sativum agglutinin, and fluoroscein conjugated acrosomal specific monoclonal antibodies.

Alternatively, light microscopy can be employed for evaluating the ability of sperm of male mammals to undergo the acrosome reaction. In this method, the capacitated sperm is stained with an acrosome specific marker and then examined using light microscopy. As in fluorescence microscopy, with light microscopy it is possible to count a representative sample of incubated capacitated sperm to measure the ability of sperm of the male mammal to undergo the acrosome reaction, thereby achieving a quantitative measure. For light microscopy the acrosome specific markers include peroxidase conjugated peanut agglutinin, Pisum sativum agglutinin, and conjugated acrosomal specific monoclonal antibodies.

An alternative method for evaluating the ability of sperm of male mammals to undergo the acrosome reaction utilizes a color reaction assay. This assay, also called a dot blot assay, employs a colorimetric substrate which yields a signal detectable by the unaided eye. In this method, a sperm sample from the male mammal is obtained, and incubated in a bromelain enzyme containing solution in a concentration effective to induce capacitation in the sperm. The sperm sample can be obtained by separating the sperm from the seminal plasma of a semen sample obtained from the male mammal. As in the first method, the bromelain enzyme containing solution optimally includes bromelain at a concentration of approximately 0.05%, and optionally one or more proteolytic enzymes, all preferably in a solution of calcium ion free modified Tyrode's solution. The incubation time optimally does not exceed approximately fifteen minutes.

The capacitated sperm is then incubated in a solution containing a calcium ionophore in a concentration effective to induce an acrosome reaction in the capacitated sperm. Following this step, the capacitated sperm is separated from the solution supernatant. The acrosomal components in the solution supernatant are then stained with an acrosome specific marker. In the preferred method, prior to staining the acrosomal components in the solution supernatant are bound to solid phase and substantially all remaining binding sites on the solid phase are blocked. The acrosomal components can then be stained. The acrosome specific markers employed include peroxidase conjugated peanut agglutinin, Pisum sativum agglutinin, and conjugated acrosomal specific monoclonal antibodies.

Accordingly, it is an object of the present invention to provide a method for determination of the ability of sperm of a male mammal to undergo the acrosome reaction.

It is a further object of the present invention to provide a means thereby for evaluating the fertility of a male mammal.

It is a further object of the present invention to provide a method for determination of the ability of sperm to undergo the acrosome reaction in which the incubation step wherein the sperm is capacitated is greatly reduced and is fifteen minutes or less.

It is a further object of the present invention to provide a method for determination of the ability of sperm to undergo the acrosome reaction which employs a colorimetric substrate, such as on a dot blot format, detectable by the unaided eye.

It is a further object of the present invention to provide a method for quantitative determination of the ability of sperm to undergo the acrosome reaction utilizing microscopy, either light or fluorescent.

It is a further object of the present invention to provide a method for determination of the ability of sperm to undergo the acrosome reaction which is simple to perform, not requiring highly trained technicians or a specialized laboratory.

Another object of the present invention is to provide a kit for determination of the ability of sperm to undergo the acrosome reaction for assessing the fertility of male mammals.

Other objects, advantages and novel features, and further scope of applicability of the present invention will be set forth in part in the detailed description to follow and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF THE PREFERRED EMBODIMENTS OF THE INVENTION (BEST MODES FOR CARRYING OUT THE INVENTION)

Using the methods of this invention, spermatozoa can be rapidly tested for ability to undergo the acrosome reaction, using fluorescence microscopy, light microscopy or color change on a dot blot assay. Enzymatic treatment of the spermatozoa has a profoundly beneficial effect in terms of capacitation time and number of spermatozoa undergoing the acrosome reaction, without adverse effect on forward motility and other parameters. Treatment with the enzyme bromelain, for as little as fifteen minutes, eliminates the four to eight hour period required to induce capacitation using physiologic saline. After treatment, sperm are fully capacitated, show excellent motility, and as many as 80% can be consistently induced to acrosome react. Bromelain is an enzyme derived from pineapple stems which previously had been used to dissolve cervical mucus in sperm antibody studies. S. Shulman et al (1980) "Studies in local immunity to sperm—Dissolving of cervical mucus by use of bromelain with retention of antibody activity" Am J Reprod Immunol 1:49–52.

The present invention, through use of bromelain or other enzymatic substances capable of capacitating sperm, presents a number of significant advantages. The total time to conduct an assay is significantly reduced. The assay is simple to perform, permitting assays in a physician's office. The percentage of sperm capacitated, as determined by the percentage able to undergo the acrosome reaction upon addition of calcium and its appropriate ionophore, is significantly higher than other capacitation methods, such as incubation in physiologic saline.

The invention is further illustrated by the following non-limiting examples.

EXAMPLE I

In this experiment, human sperm samples were tested for their ability to undergo the acrosome reaction, using fluoroscein isothiocyanate (FITC) analysis for fluorescence microscopy in which peanut agglutinin (PNA) was used as the marker to detect and measure the percentage of spermatozoa undergoing the acrosome reaction. The following reagents were used in this example:

MTS: (Modified Tyrode's Solution) 2.8 mM KCI; 1.17M NaCl; 0.5 MM $MgCl_2 \times 6H_2O$; 0.36 mM $NaH_2PO_4 \times 1H_2O$; 1.8 mM $CaCl_2$; 12 mM $NaHCO_3$; 0.25 mM pyruvic acid; 5.5 mM glucose; 3.3 mM HEPES; in double distilled water, pH 7.74

MTSF: (Modified Tyrode's Solution, calcium ion Free) same as above, with no $CaCl_2$ MTSF/BSA: MTSF+3% bovine serum albumin (Sigma)

MTSF/bromelain: MTSF+0.05% bromelain (Sigma B2252), filtered and dialyzed

MTS/Ionophore: MTS+10 µg/ml A23187 Ionophore (Sigma)

PLO for slide coating: 0.1% poly-L-ornithine (Sigma P3655) in DDW.

Slides: 10 well microslide with masking (Carlson Scientific)

FITC Reagent: MTSF/BSA+10 µg/ml PNA/FITC (EY Labs F2301)

In the assay, the following steps were employed:

1) Collect sperm sample in sterile container and allow to liquefy (30 minute period).
2) Mix sample with 10 ml MTSF and centrifuge at 400×g for 5 minutes.
3) Discard supernatant, resuspend pellet in 5 ml MTSF/0.05% bromelain. Divide into two equal portions. Incubate in water bath at 37° C. for 15 minutes, centrifuge both at 400×g for 5 minutes, and resuspend in 5 ml MTSF.
4) Centrifuge, discard supernatants, and resuspend one pellet (test pellet) in 0.2 ml MTS/Ionophore. Resuspend other pellet in 0.2 ml MTS (negative control pellet).
5) Incubate 60 minutes and centrifuge at 400×g for 5 minutes.
6) Pellets of Ionophore-induced sperm are resuspended in MTSF, washed once, and suspended at a concentration from $1 \times 10^6$/ml to $10 \times 10^6$/ml in MTSF.
7) 25 µl of sperm suspension is placed on each well of a spot slide and allowed to air dry at 37° C. (Slides are coated with PLO (poly-L-ornithine) for 1 hour and rinsed 3× with MTSF prior to use.)
8) After drying, slides are immersed in absolute methanol for 5 minutes, acetone for 5 minutes and air dried.
9) To stain, slides are rehydrated in MTSF/BSA for 1–2 hours, and 25 µl of FITC reagent applied to each well. Slides are kept in a moist chamber to prevent evaporation until the staining is complete.
10) After 1 hour slides are rinsed 4× with MTSF, coverslipped and examined by fluorescence microscopy at 400× magnification. Acrosomes appear bright green.

Using the foregoing method, ten presumptively normal human donor sperm samples were tested, and the mean percentage of acrosomes reacted was 71%, with a standard deviation of ±10.2%, and an absolute range of 43% to 78%. The negative control sample, in which no ionophore was added, as described in step 4, yielded a mean percentage of acrosome reacted of 24%, with a standard deviation of ±7.5%, and an absolute range of 12% to 37%.

EXAMPLE II

Using the method of Example I, assays were conducted on the same day on two different individuals, one a normal volunteer and one an individual with a known problem with fertility. Table 1 shows the results of the fluorescence microscopy.

TABLE 1

| COMPARISON OF A SPERM ASSAY BETWEEN NORMAL AND ABNORMAL DONOR | | |
|---|---|---|
| | Normal | Abnormal |
| Concentration of Cells/ml × $10^6$ | 120.0 | 36.7 |
| Percent Motility | | |
| No Treatment | 59.9% | 44.4% |
| After Bromelain (0.05%) | 58.1% | 17.5% |
| After Ca-Ionophore | 3.1% | 0.0% |
| Percent Acrosome Reaction | | |
| Total Cells Reacting | 76.0% | 41.0% |
| Background | 17.0% | 35.0% |
| Net Increase | 59.0% | 7.0% |

EXAMPLE III

Using the method of Example I, sperm were treated with bromelain in concentrations ranging from 0.05% to 5.0% before adding the ionophore to induce the acrosome reaction. Thus, in step 3 the bromelain concentration was altered as reflected below in Table 2.

TABLE 2

THE EFFECT OF BROMELAIN CONCENTRATION ON PERCENT ACROSOME ACTIVATION OF SPERM FROM NORMAL MALE DONORS

| PERCENT BROMELAIN | NUMBER OF DONORS TESTED | PERCENT ACROSOME ACTIVATION[1] |
|---|---|---|
| 5.00% | 6 | 71% |
| 2.50% | 12 | 72% |
| 1.25% | 4 | 52% |
| 1.00% | 12 | 68% |
| 0.50% | 10 | 72% |
| 0.10% | 10 | 71% |
| 0.05% | 10 | 71% |
| 0.00% | 10 | 26% |

[1] Each individual sample was tested in at least duplicate; some were tested four times and some eight times. The mean score for each individual donor was then averaged, to yield an average percent acrosome activation.

EXAMPLE IV

This example illustrates the process of this invention using a dot assay, in which the reaction takes place on a nitrocellulose membrane in a dip-stick type apparatus. The assay results are determined by the human eye based on color change. The following reagents, in addition to those set forth in Example I, are employed:

Acrosomal marker: PNA/Peroxidase—MTSF/BSA+10 μg/ml PNA/Peroxidase (EY Labs H2301)

Substrate: 2.8 mM 4-chloro-1-naphthol (Sigma) (30 mg 4-chloro-1-naphthol+10 ml absolute methanol+60 ml PBS+75 μl $H_2O_2$)

Membrane disc: Pall Immunodyne Immunoaffinity Membrane, P/N:BIA0045HC8125, 0.45 micron Membrane holder: Single well membrane holder (RhoMed Inc.)

To conduct the assay, steps 1 through 5 of Example I are followed. The pellet resulting from centrifugation in step 5 can be used for fluorescence microscopy assay as in Example I, or the supernatant used for the dot assay, following these steps:

6) Add supernatants to test well or negative control well containing nitrocellulose disc. Allow to incubate 60 minutes.

7) Wash wells thoroughly with MTSF (3×–5 minutes each), add MTSF/3% BSA (blocking reagent), and incubate for 30 minutes.

8) Wash wells thoroughly with MTSF (3×–5 minutes each), and add acrosomal marker (PNA/peroxidase). Incubate 45 minutes.

9) Wash wells thoroughly with MTSF (3×–5 minutes each), and add substrate. Color should develop within 15 minutes, indicating a positive acrosome reaction.

The normal and abnormal donor sperm samples of Example II were employed in this Example, with the supernatants assayed as set forth above, and the pellets assayed as set forth in Example II. With the normal subject, the difference between the negative control background to which no ionophore has been added and the test sample was pronounced; with the abnormal subject, the difference between the background and test sample was minor. The color reaction of the normal subject test sample was significantly more intense than the color reaction of the abnormal subject test sample.

EXAMPLE IV

This example illustrates the use of a positive control in the dot blot assay of Example III. In this example, three dipsticks are employed, one consisting of the negative control background to which no ionophore has been added, the second consisting of the test sample, and the third consisting of a standardized sample of pooled normal sperm and liquid nitrogen treated pooled normal sperm adjusted so as to give a 50% acrosome reaction. Alternatively, a three well dipstick, rather than three single well dipsticks, may be employed.

EXAMPLE V

In this experiment, human sperm samples were tested for their ability to undergo the acrosome reaction, using light microscopy analysis. The method of Example I was employed, with modification of the reagents and method as follows. The following additional reagents were used in this example:

Peroxidase Reagent: MTSF/BSA+10 μg/ml PNA/Peroxidase (EY Labs H2301)

Substrate: 2.8 mM 4-chloro-1-naphthol (Sigma) (30 mg 4-chloro-1-naphthol+10 ml absolute methanol+60 ml PBS+75 μl $H_2O_2$)

In the assay, steps 1) through 8) of Example I were employed, with the following new steps 9), 10), and 11):

9) To stain, slides are rehydrated in MTSF/BSA for 1–2 hours, and 25 μl of Peroxidase Reagent applied to each well.

10) After 1 hour, slides are rinsed 4 times with MTSF, and substrate added.

11) After 15–30 minutes incubation with the substrate, slides are rinsed thoroughly with double distilled water, coverslipped and examined by bright field or phase contrast microscopy at 400× magnification.

The preceding examples can be repeated with similar success by substituting the generically or specifically described reactants and/or operating conditions of this invention for those in the preceding example. In particular, incubation times may be varied; wash steps may be eliminated or increased; different reagents may be employed for the incubation and wash steps; different calcium ionophores, and in differing concentrations, may be employed; other acrosomal markers, including monoclonal antibodies, may be employed; other fluorescence or color indicator systems may be employed; and, for the dot blot format, different membrane systems may be employed. The foregoing are merely illustrative, and other equivalent embodiments are possible and contemplated.

Although the invention has been described with reference to these preferred embodiments, other embodiments can achieve the same results. Variations and modifications of the present invention will be obvious to those skilled in the art and it is intended to cover in the appended claims all such modifications and equivalents.

The invention claimed is:

1. A method for evaluating the ability of sperm of male mammals to undergo the acrosome reaction, comprising the steps of:
   a) obtaining a sperm sample from a male mammal;
   b) incubating the sperm in a bromelain enzyme containing solution in a concentration sufficient to induce capacitation in the sperm;
   c) incubating the capacitated sperm in a solution capable of inducing an acrosome reaction in the capacitated sperm; and d) examining a representative sample of incubated capacitated sperm to determine the ability of sperm of the male mammal to undergo the acrosome reaction.

2. The method of claim 1 wherein the obtaining of a sperm sample in step a) comprises separating the sperm from seminal plasma of a semen sample obtained from the male mammal.

3. The method of claim 1 wherein incubating step b) comprises incubating the sperm in a bromelain enzyme containing solution at a concentration whereby there is no adverse effect on the sperm.

4. The method of claim 3 wherein the bromelain enzyme containing solution comprises a solution having a concentration of bromelain of approximately 0.05%.

5. The method of claim 1 wherein incubating step b) comprises incubating the sperm in a bromelain enzyme containing solution comprising bromelain and at least one proteolytic enzyme.

6. The method of claim 3 wherein the bromelain enzyme containing solution further comprises calcium ion free modified Tyrode's solution.

7. The method of claim 1 wherein the incubating step b) comprises an incubation time that does not exceed approximately fifteen minutes.

8. The method of claim 1 wherein the incubating step c) comprises incubating the capacitated sperm in a solution containing the calcium ionophore A23187 in a concentration sufficient to induce an acrosome reaction in the capacitated sperm.

9. The method of claim 1 wherein the examining step d) comprises using fluorescence microscopy for evaluating the ability of sperm of male mammals to undergo the acrosome reaction by staining the capacitated sperm with an acrosome specific fluoroscein marker and examining the stained acrosome reacted capacitated sperm using fluorescence microscopy.

10. The method of claim 9 wherein the examination of the stained acrosome reacted capacitated sperm using fluorescence microscopy further comprises the step of counting a representative sample of incubated capacitated sperm to measure the ability of sperm of the male mammal to undergo the acrosome reaction.

11. The method of claim 9 wherein the acrosome specific fluoroscein marker comprises at least one member selected from the group consisting of fluoroscein conjugated peanut agglutinin, fluoroscein conjugated Pisum sativum agglutinin, and fluoroscein conjugated acrosomal specific monoclonal antibodies.

12. The method of claim 1 wherein the examining step d) comprises using light microscopy for evaluating the ability of sperm of male mammals to undergo the acrosome reaction by staining the capacitated sperm with an acrosome specific marker and examining the stained acrosome reacted capacitated sperm using light microscopy.

13. The method of claim 12 wherein the examination of the stained acrosome reacted capacitated sperm using light microscopy further comprises the step of counting a representative sample of incubated capacitated sperm to measure the ability of sperm of the male mammal to undergo the acrosome reaction.

14. The method of claim 12 wherein the acrosome specific marker comprises at least one member selected from the group consisting of peanut agglutinin, Pisum sativum agglutinin, and conjugated acrosomal specific monoclonal antibodies.

15. A method for color reaction assay for evaluating the ability of sperm of male mammals to undergo the acrosome reaction, the method comprising the steps of:
a) obtaining a sperm sample from a male mammal;
b) incubating the sperm in a bromelain enzyme containing solution in a concentration sufficient to induce capacitation in the sperm;
c) incubating the capacitated sperm in a solution capable of inducing an acrosome reaction in the capacitated sperm;
d) separating the capacitated sperm from the solution supernatant;
e) staining the acrosomal components in the solution supernatant with an acrosome specific marker; and
f) colorimetrically examining the solution supernatant to determine the ability of sperm of the male mammal to undergo the acrosome reaction.

16. The method of claim 15 wherein the obtaining of a sperm sample in step a) comprises separating the sperm from seminal plasma of a semen sample obtained from the male mammal.

17. The method of claim 15 wherein incubating step b) comprises incubating the sperm in a bromelain enzyme containing solution at a concentration whereby there is no adverse effect on the sperm.

18. The method of claim 17 wherein the bromelain enzyme containing solution comprises a solution having a concentration of bromelain of approximately 0.05%.

19. The method of claim 15 wherein incubating step b) comprises incubating the sperm in a bromelain enzyme containing solution comprising bromelain and at least one proteolytic enzyme.

20. The method of claim 17 wherein the bromelain enzyme containing solution further comprises calcium ion free modified Tyrode's solution.

21. The method of claim 15 wherein the incubating step b) comprises an incubation time that does not exceed approximately fifteen minutes.

22. The method of claim 15 wherein the incubating step c) comprises incubating the capacitated sperm in a solution containing the calcium ionophore A23187 in a concentration sufficient to induce an acrosome reaction in the capacitated sperm.

23. The method of claim 15 wherein the acrosome specific marker comprises at least one member selected from the group consisting of peanut agglutinin, Pisum sativum agglutinin, and conjugated acrosomal specific monoclonal antibodies.

24. A method of inducing capacitation in sperm of male mammals, comprising incubating the sperm in a bromelain enzyme containing solution in a concentration sufficient to induce capacitation in the sperm.

* * * * *